(12) United States Patent
Jiao et al.

(10) Patent No.: US 9,115,177 B2
(45) Date of Patent: Aug. 25, 2015

(54) PREPARATION METHOD OF MICAFUNGIN SODIUM

(75) Inventors: Guangjun Jiao, Shanghai (CN); Shidong Liu, Shanghai (CN); Bingming He, Shanghai (CN); Zhijun Tang, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/116,947

(22) PCT Filed: May 11, 2012

(86) PCT No.: PCT/CN2012/075339
§ 371 (c)(1),
(2), (4) Date: Jan. 2, 2014

(87) PCT Pub. No.: WO2012/152225
PCT Pub. Date: Nov. 15, 2012

(65) Prior Publication Data
US 2014/0114049 A1  Apr. 24, 2014

(30) Foreign Application Priority Data
May 12, 2011 (CN) .......................... 2011 1 0121705

(51) Int. Cl.
*C07K 1/113* (2006.01)
*C07K 7/56* (2006.01)
*C07K 1/14* (2006.01)
*C07D 413/12* (2006.01)

(52) U.S. Cl.
CPC ............... *C07K 1/14* (2013.01); *C07D 413/12* (2013.01); *C07K 1/113* (2013.01); *C07K 7/56* (2013.01)

(58) Field of Classification Search
None
See application file for complete search history.

(56) References Cited

U.S. PATENT DOCUMENTS

2014/0371422 A1* 12/2014 Gunnes et al. ................ 530/329

FOREIGN PATENT DOCUMENTS

WO    WO 9611210        4/1996
WO    WO 2004014879     2/2004
WO    WO 2012143293 A1 * 10/2012

OTHER PUBLICATIONS

PCT International Search Report and Written Opinion dated Aug. 23, 2012 issued in PCT/CN2012/075339 (WO/2012/152225).

Ohigashi et al. (2006) "Process development of micafungin. a novel lipopeptide antifungal agent." *Yuki Gosei Kagaku Kyokaishi*.. 64(12): 1294-1303.

Tomishima et al. (2008) "Novel echinocandin antifungals. Part 2: Optimization of the side chain of the natural product FR901379. Discovery of micafungin" *Bioorganic & Medicinal Chemistry Letters* 18: 2886-2890.

* cited by examiner

*Primary Examiner* — Jeffrey E Russel
(74) *Attorney, Agent, or Firm* — Tom Hunter; Weaver Austin Villeneuve & Sampson LLP (57) ABSTRACT

The method of the preparation of micafungin sodium comprises the step of mixing the weak base and the aqueous solution containing micafungin acid (the structure is illustrated by formula I) or the mixed aqueous solution containing the compound of formula I and organic solvent in order to obtain the sodium salt of micafungin (the structure is illustrated by formula II).

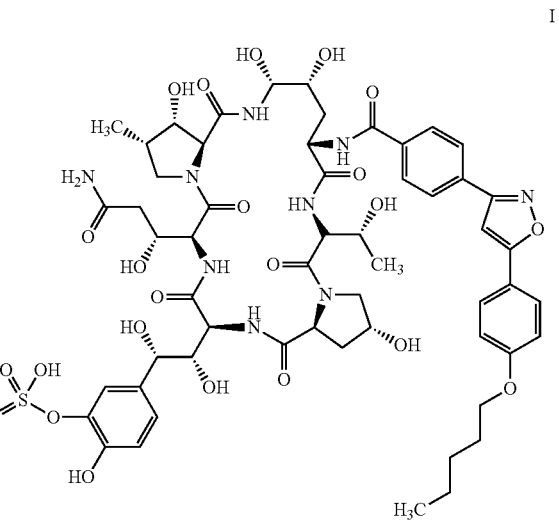

17 Claims, 4 Drawing Sheets

PREPARATION METHOD OF MICAFUNGIN SODIUM

CROSS-REFERENCE TO RELATED APPLICATIONS

This application is a 371 National Phase of PCT/CN2012/075339, filed on May 11, 2012, which claims benefit of and priority to CN 201110121705.5, filed on May 12, 2011, which is incorporated herein by reference in its entirety for all purposes.

FIELD OF INVENTION

The invention involves purification of compounds, particularly a preparation method for Micafungin sodium.

BACKGROUND

Micafungin is a second clinically applied pneumocandins drug after caspofungin. It mostly inhibits the synthesis of the main ingredient of fungi cell walls, i.e. 1,3-β-D-dextran, and therefore disrupts the formation of fungi cell walls and influences cell morphology and osmotic pressure thereof, thus leading to cytolysis and cell death. Micafungin is mainly used for treating deep fungi infections such as that from *Monilia, Aspergillus*, etc. In particular, it is used for treating fungi infections in patients with low immunity, such as chemotherapy patients, AIDS patients, etc. Clinically, it is also used in combination with amphotericin and triazole anti-fungi drugs.

Micafungin is developed by Fujisawa Pharmaceutical, under the trade name of Mycamine. Micafungin is on the market as sodium form, the formula of which is shown as follows.

WO9611210 and WO2004014879 have reported processes for synthesis and purification of micafungin.

WO9611210 has reported a method for obtaining the sodium salt by using cation exchange resin (DOWEX-50WX4). It is impossible to control the pH value of the product using said method. In addition, this method only applies to small-scale preparation. It is hardly suited for expanded scale of production and quality of products thereof is unmanageable.

Figure 2:
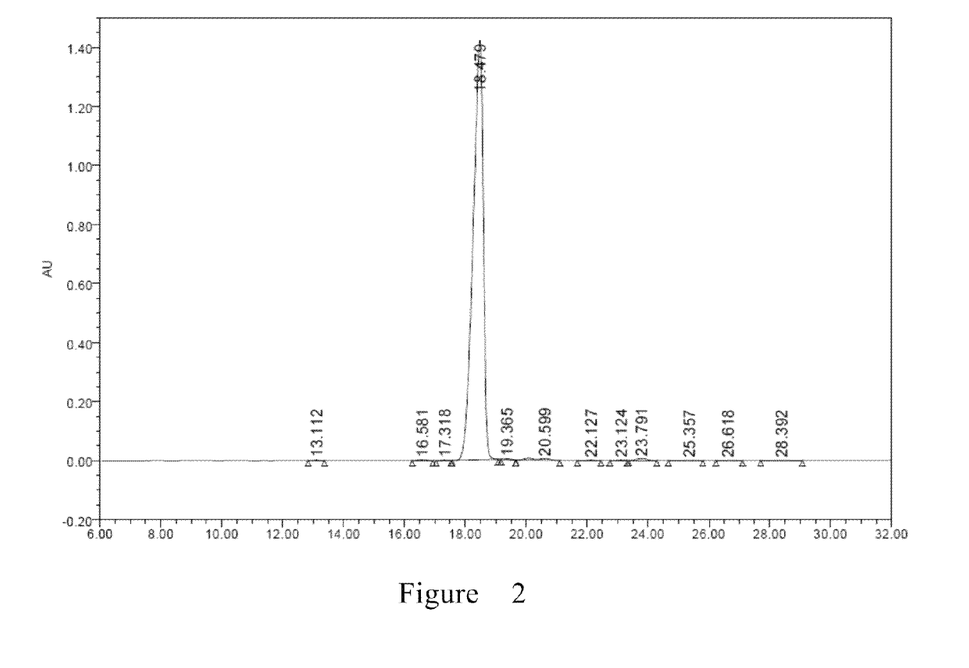
FIG. 2 is the HPLC chromatogram of formula II compound prepared in Comparative Example 2, wherein parameters of the related peaks, such as Retention Time and areas thereof are listed in the following table.
Figure 3:
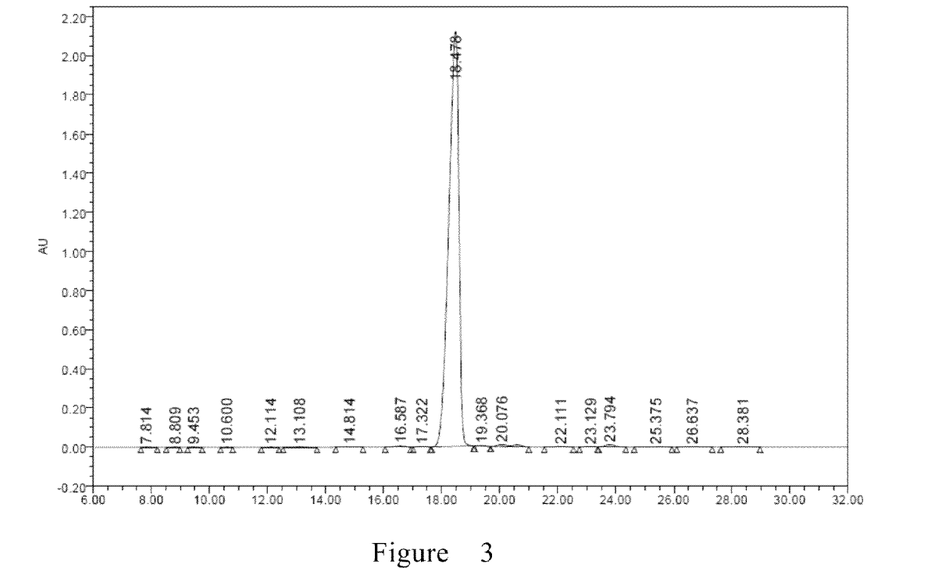
FIG. 3 is the HPLC chromatogram of formula II compound prepared in Comparative Example 2, wherein parameters of the related peaks, such as Retention Time and areas thereof are listed in the following table.

WO2004014879 has reported a method using 0.1 mol/L NaOH solution to adjust pH value to 6-8. The Inventors have performed multiple experiments using methods reported in the literature and have discovered that adjusting the pH value according to said method leads to a significant rise in the content of impurity from micafungin degradation, as is shown in FIGS. 2 and 3, thereby considerably increasing the difficulty in the subsequent separation and purification and it is difficult to prepare micafungin sodium of high purity. Hence, the method can not fulfil the requirements for industrialized manufacture.

Therefore, it is urgent to develop a method for the preparation of micafungin sodium in order to obtain micafungin sodium of high purity.

SUMMARY OF INVENTION

The Invention aims at providing a convenient method for the preparation of micafungin sodium.

Another objective of the Invention is to provide a preparation method of micafungin sodium which is adapted for the industrial production.

In the first aspect of the Invention, a preparation method for the compound of formula II is provided, comprising steps as follows:

mixing a weak base solution with a water solution containing the compound of formula I or a mixture solution of water and organic solvent(s) containing the compound of formula I, and thereby obtaining the compound of formula II;

In the aforementioned preparation method, the cation in the weak base solution is sodium ion; pKA value of the conjugate acid corresponding to the weak base is 4-11, preferably 5-8.

In the aforementioned preparation method, the weak base is organic weak base solution, inorganic weak base solution, or combination thereof. The organic weak base is selected from the group consisting of disodium hydrogen citrate, sodium citrate, sodium acetate, sodium propionate, sodium butyrate, sodium isobutyrate, sodium tartrate, sodium oxalate, sodium benzoate, sodium sorbate, sodium malate, monosodium succinate, disodium succinate and combinations thereof; preferably, the organic weak base is selected from the group consisting of disodium hydrogen citrate, sodium citrate, sodium acetate and combinations thereof. The inorganic weak base is selected from the group consisting of sodium bicarbonate, sodium carbonate, disodium hydrogen phosphate, sodium borate, sodium sulfite, sodium hydrosulfide and combinations thereof; preferably, the inorganic weak base is sodium bicarbonate.

In the aforementioned preparation method, the pH value of the solution obtained from mixing the weak base solution with the water solution containing the compound of formula I is 4.0-7.0, preferably 4.0-6.0, most preferably 4.5-5.5.

In the aforementioned preparation method, the pH value of the solution obtained from mixing the weak base solution with the mixture solution of water and organic solvent(s) containing the compound of formula I is 4.0-7.0, preferably 4.0-6.0, most preferably 4.5-5.5.

In the aforesaid preparation method, the concentration of the weak base solution is 0.001-1 mol/L; preferably, 0.01-0.5 mol/L.

In the aforesaid preparation method, the organic solvent is selected from alcohols or acetonitrile, preferably a C1-C4 alcohol, most preferably selected from the group consisting of methanol, ethanol, isopropanol, n-propanol, n-butanol, sec-butanol, t-butanol and combinations thereof.

In another embodiment, a preparation method for the compound of formula II is provided in the Invention, comprising the following steps:

at room temperature, adding the weak base solution to the water solution containing the compound of Formula I or the mixture solution of water and organic solvent(s) containing the compound of Formula I, adjusting the pH value of the obtained solution, thereby obtaining the compound of Formula II; and said addition is performed slowly with stirring.

Thus, the Invention provided a preparation method for micafungin sodium so as to obtain micafungin sodium of high purity.

DESCRIPTION OF FIGURES

| Retention Time | Area | Height | Percentage of Area |
|---|---|---|---|
| 16.492 | 31807 | 1659 | 0.15 |
| 18.227 | 20816865 | 967335 | 99.55 |
| 20.471 | 63295 | 3710 | 0.30 |

| Retention Time | Area | Height | Percentage of Area |
|---|---|---|---|
| 13.112 | 21149 | 1395 | 0.06 |
| 16.581 | 61878 | 3000 | 0.18 |
| 17.318 | 21882 | 1309 | 0.06 |
| 18.479 | 33290939 | 1423115 | 98.01 |
| 19.365 | 38294 | 2451 | 0.11 |
| 20.599 | 289113 | 6553 | 0.85 |
| 22.127 | 28987 | 1280 | 0.09 |
| 23.124 | 17974 | 976 | 0.05 |
| 23.791 | 140287 | 6104 | 0.41 |
| 25.357 | 15057 | 439 | 0.04 |
| 26.618 | 9618 | 399 | 0.03 |
| 28.392 | 31413 | 1013 | 0.09 |

| Retention Time | Area | Height | Percentage of Area |
|---|---|---|---|
| 7.814 | 20127 | 1462 | 0.04 |
| 8.809 | 7857 | 724 | 0.01 |
| 9.453 | 16198 | 1238 | 0.03 |
| 10.600 | 4883 | 420 | 0.01 |
| 12.114 | 7499 | 483 | 0.01 |
| 13.108 | 48805 | 2465 | 0.09 |
| 14.814 | 17647 | 893 | 0.03 |
| 16.587 | 111648 | 5015 | 0.21 |
| 17.322 | 42997 | 2356 | 0.08 |
| 18.478 | 51279846 | 2121252 | 97.67 |
| 19.368 | 64987 | 4085 | 0.12 |
| 20.076 | 443712 | 10219 | 0.85 |
| 22.111 | 52715 | 2171 | 0.10 |
| 23.129 | 34128 | 1790 | 0.06 |
| 23.794 | 253956 | 10958 | 0.48 |
| 25.375 | 25571 | 756 | 0.05 |
| 26.637 | 23028 | 707 | 0.04 |
| 28.381 | 49128 | 1492 | 0.09 |

| Retention Time | Area | Height | Percentage of Area |
|---|---|---|---|
| 16.490 | 26352 | 1220 | 0.20 |
| 17.214 | 8971 | 547 | 0.07 |
| 18.227 | 13162110 | 614407 | 99.17 |
| 19.255 | 8117 | 545 | 0.06 |
| 20.468 | 56926 | 2842 | 0.43 |
| 23.620 | 9839 | 512 | 0.07 |

| Retention Time | Area | Height | Percentage of Area |
|---|---|---|---|
| 16.492 | 28624 | 1585 | 0.14 |
| 18.227 | 20543002 | 963168 | 99.52 |
| 20.471 | 69682 | 3906 | 0.34 |

MODES FOR CARRYING OUT THE INVENTION

Through intensive research, the inventors have discovered that by adding inorganic weak base solution, organic weak base solution or combination thereof into a water solution containing the compound of formula I or a mixture solution of water and organic solvent containing the compound of formula I, and adjusting pH value of the solution to 4.0-7.0, a solution of micafungin sodium of high purity can be prepared. The method is easily operated and of high reproducibility, and the quality of product is high, therefore, the method is well suited for industrial production.

Process of Invention and Analysis of the Principle

Figure 6:
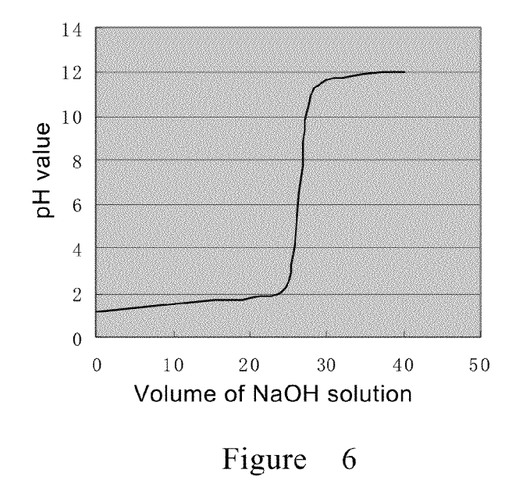
FIG. 6 illustrates the pH value curve of titrating strong acid (hydrochloric acid) with strong base (NaOH solution).

Generally, there are two ways for preparing acid into sodium salt. One is exchange using cationic resin; the other is via adjusting pH value. Virtually, preparing sodium salt by adjusting pH value is a process of neutralization reaction between acid and base. It includes two types of reactions, i.e. the reaction between strong acid and strong base, and the reaction between strong acid and weak base. If strong base solution is added into strong acid solution for adjusting pH value, there is a sharp change in the pH value of the solution (the change of pH value is illustrated in FIG. 6), and the pH value will be instantly altered by 8. Therefore in the practical production, it is hard to control the pH value and a slightest mistake could lead to an overregulated pH value. In WO2004014879, a 0.1 mol/L NaOH solution was used to adjust pH value to 6-8 for obtaining formula II compound. It was actually a reaction between strong acid and strong base. The compound of formula I contains benzene sulfonic acid groups and pKa values of benzene sulfonic acid compounds are generally less than 1, therefore the compound is strong acid compound (See FIG. 1). Therefore, theoretically, the method using NaOH solution to adjust pH values for obtaining sodium salt is unsuitable for preparation of formula II compound.

TABLE 1 pKa values of Compounds of Benzene Sulfonic Acid

| Compounds of Benzene Sulfonic Acid | pKa |
| --- | --- |
| benzene sulfonic acid | 0.70 |
| toluene sulfonic acid | −2.58 |
| 4-hydroxy benzene sulfonic acid | −2.19 |
| 1-naphthalene sulfonic acid | 0.57 |

Figure 1:
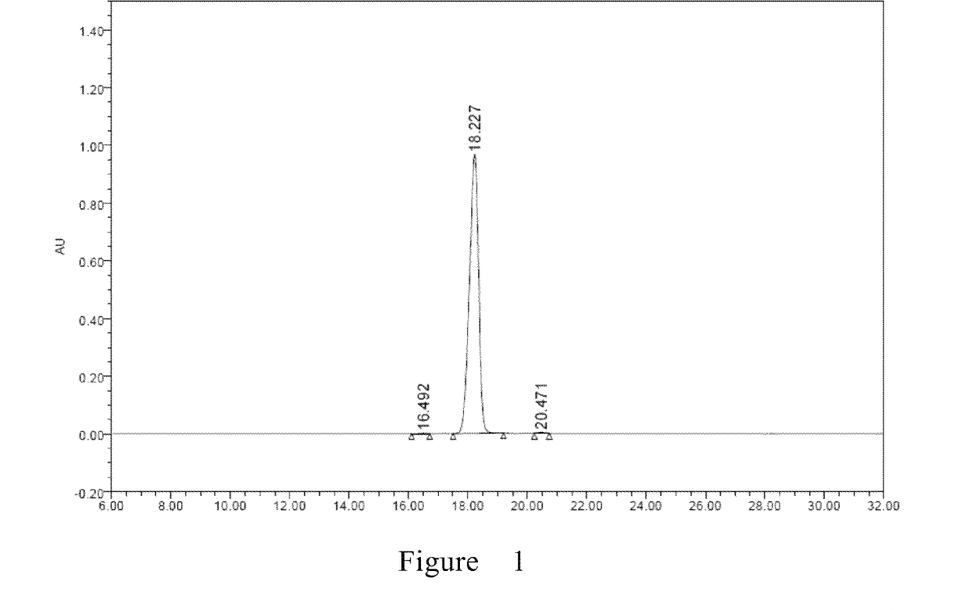
FIG. 1 is the HPLC chromatogram of formula I compound in Example 1, wherein parameters of the related peaks, such as Retention Time and areas thereof are listed in the following table.

The inventors have repeated the method reported in WO2004014879 for multiple times and analyzed and validated the reported method from the point of view of local pH value. The inventors have found that during the course of pH adjusting, regarding the whole solution system, 0.1 mol/L NaOH solution has a relatively low concentration and the overall pH value can be managed at 6-8, however, during the course of adding NaOH solution dropwise, the local base concentration gets too high, i.e. local pH value in the solution gets overly high, therefore, partial degradation occurred in micafungin, hence the impurity content is much too high. See FIGS. 1, 2 and 3. FIG. 1 shows the HPLC purity of formula I compound before pH adjustment. FIGS. 2 and 3 show HPLC purities after formula I compound is adjusted in pH value with 0.1 mol/L NaOH solution, in which obvious degradation can be found.

Figure 7:
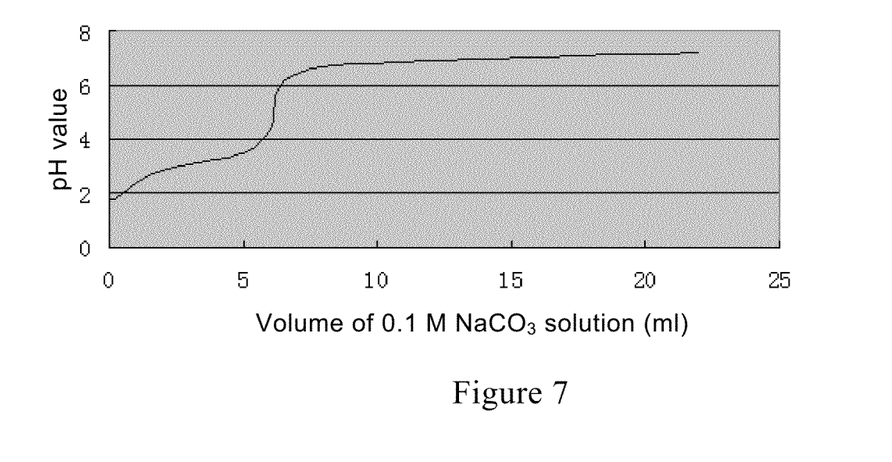
FIG. 7 illustrates the pH value curve of titrating micafungin solution with 0.1 M solution of sodium bicarbonate.

In order to avoid the aforesaid prominent defects, the inventors have conducted further and intensive researches and have unexpectedly found that by using inorganic weak base solution, organic weak base solution or combinations thereof to adjust pH value of solution of formula I compound, compound of formula II can be obtained without generating extra impurities. The inventors have conducted in-depth analysis on the cause of the sound result from the aforesaid weak base solution. First of all, there exists within the weak base solution an ionization equilibrium. The molecules are in a state of incomplete ionization and possess a certain degree of buffer capacity. Therefore, when adjusting the pH value, there is not an obvious pH surge, as is shown in FIG. 7. While using 0.1 M $NaHCO_3$ solution to titrate the solution of micafungin, the pH changes slowly and there is not an obvious pH surge, and the pH value can be stably remained at 7, thus facilitating the pH control during the practical production. Secondly, compared with the strong base solution, weak base solutions of the same concentration per se have lower pH values. During the course of adding the weak base solution into the solution of formula I compound, the local pH value won't readily rise. Therefore, using weak base solution to adjust the pH of the solution of formula I compound for preparing sodium salt is a method much suited for the preparation of formula II compound. In addition, the inventors, via further in-depth studies, further unexpectedly found that the concentration of weak base solution will also influence the sodium salt preparation via adjustment of pH. In theory, the lower the concentrations of weak bases, the better the results, however, overly low concentration obviously does not conform to the practical requirements in the production. Based on the experiment data, the concentration of the weak base is preferably at 0.001-1 mol/L, for achieving the best effects.

The inventors have also conducted further researches and discussions for determining the pKa values of the conjugate acid corresponding to the weak base. The test results showed that the pKa value of the conjugate acid corresponding to the weak base is preferably at 4-11, most preferably 5-8. The pKa value is a particular balance constant which represents the capacity of an acid to dissociate hydrogen ion. The lower the pKa value, the strong its capacity to offer proton, hence a stronger acidity, a smaller alkalinity of its corresponding conjugate base has, and vice versa. The equation to calculate pKa is: $pKa = -1g[H^+][A^-]/[HA]$ (HA stands for weak acid, $H^+$ is the hydrogen ion ionized from the weak acid HA, $A^-$ is an anion ionized from the weak acid HA). The compound of Formula I is a sulfonic acid compound of strong acid type. In a solution, it is almost completely ionized, and the pKa thereof is generally lower than 1. Therefore, it can facilitate the reaction to take place when encounter a weak base (conjugate acid pKa=4). When the compound of formula I reacts with the weak base and generates a weak acid with the pKa value of 4, via the aforesaid equation of pK, it can be calculated that the concentration of weak acid [HA] generated in the solution is 100 times the concentration of $[H^+]$ or $[A^-]$. Since the concentration of residue $[H^+]$ is comparable with that of the residue formula I compound, the concentration of generated weak acid [HA] is 100 times higher than that of the residue [formula I compound], that is, 99% of the formula I compound has been transformed into the form of sodium salt. When formula I compound reacted with the weak base and generates a weak acid with pKa of 11, it can be calculated via the aforesaid equation that the concentration of the weak acid [HA] generated in the solution is $3.16 \times 10^5$ times that of $[H^+]$ or $[A^-]$. Likewise, 99.99% of formula I compound has transformed into a sodium salt form. Lastly, based on the experiment results, it is verified that pKa value of the conjugate acid of the weak base should be chosen at 4-11, for achieving the optimum effects.

The inventors have also discovered via experiments on stability of micafungin in solutions with different pH that micafungin has poor stability in a solution with high pH value. Generally its stability is good under pH 4.0-7.0, more stable at 4.0-6.0, most stable under 4.5-5.5. Therefore, while adjusting the pH value of micafungin, it is necessary to consider adjusting pH value of the solution. WO2004014879 reported that the pH can be adjusted at 6-8, which is obviously unreasonable. The inventors have discovered through experiments that, when the pH of solution is adjusted to 7, the stability is relatively good and there is no obvious degradation of the compound. According to the equation ($pH = -1\ g[H]^+$), if the initial concentration of formula I compound is 0.01 mol/L, when pH is 4, $H^+$ concentration in the solution is lower than 0.0001 mol/L. In addition, since formula I compound is a sulfonic acid compound of strong acid type, it is almost completely ionized in the solution. Therefore, when pH is adjusted to 4, the concentration of residue formula I compound is lower than 0.0001 mol/L, that is, more than 99% of formula I compound have been transformed into formula II compound. Therefore, when pH value is adjusted to 4, it can be ensured that formula I compound is transformed into a form of sodium salt. In combination with the stability data of formula II compound in solutions of different pH, it is preferably to adjust the pH value of the solution to 4.0-7.0, more preferably 4.0-6.0, most preferably 4.5-5.5.

In conclusion, the inventors have, through meticulous studies on principles of acids and bases and via a considerable amount of screening experiments, unexpected found that using weak base solution to adjust pH value of micafungin solution can effectively prevent micafungin from generating new impurities, thereby smoothly attaining the transformation of micafungin from acid type to sodium type, greatly reducing the complexity of subsequent purification steps, effectively increasing the production rate and purity of the final product of micafungin.

Preparation Method for Compound of Formula II

The invention provided a preparation method for the compound of formula II, which comprises the following steps:

mixing a weak base solution with a water solution containing the compound of formula I or a mixture solution of water and organic solvent(s) containing the compound of formula I, thereby obtaining the compound of formula II.

The organic solvent is selected from alcohols or acetonitrile, preferably a C1-C4 alcohol, most preferably selected from the group consisting of methanol, ethanol, isopropanol, n-propanol, n-butanol, sec-butanol, t-butanol and combinations thereof.

The pH value is 4.0-7.0, preferably 4.0-6.0, most preferably 4.5-5.5.

The weak base is a base that is ionized incompletely in the water solution, i.e., protonation thereof is incomplete. pKa value of the corresponding conjugate acid thereof is 4-11, preferably 5-8 (See Table 2 below); It mainly comprises organic and inorganic weak bases. The organic weak base is selected from the group consisting of disodium hydrogen citrate, sodium citrate, sodium acetate, sodium propionate, sodium butyrate, sodium isobutyrate, sodium tartrate, sodium oxalate, sodium benzoate, sodium sorbate, sodium malate, monosodium succinate, disodium succinate and combinations thereof, preferably selected from the group consisting of disodium hydrogen citrate, sodium citrate, sodium acetate and combinations thereof. The inorganic weak base is selected from the group consisting of sodium bicarbonate, sodium carbonate, disodium hydrogen phosphate, sodium borate, sodium sulfite, sodium hydrosulfide and combinations thereof, preferably sodium bicarbonate.

TABLE 2 pKa Values of Conjugate Acids for the Aforementioned Weak Bases

| Conjugate Acid | pKa1 | pKa2 | pKa3 |
| --- | --- | --- | --- |
| citric acid | 3.13$^a$ | 4.76 | 6.40 |
| acetic acid | 4.76 | | |
| propionic acid | 4.87 | | |
| butyric acid | 4.82 | | |
| isobutyric acid | 4.69 | | |
| tartaric acid | 3.04$^a$ | 4.37 | |
| oxalic acid | 1.27$^a$ | 4.27 | |
| benzoic acid | 4.20 | | |
| sorbic acid | 4.76 | | |
| malic acid | 3.40$^a$ | 5.13 | |
| succinic acid | 4.21 | 5.64 | |
| carbonic acid | 6.38 | 10.25 | |
| phosphoric acid | 2.12$^a$ | 7.2 | 12.36$^a$ |
| boric acid | 9.24 | 12.74$^a$ | 13.80$^a$ |
| sulfurous acid | 1.90$^a$ | 7.20 | |
| hydrosulfuric acid | 6.88 | 14.15$^a$ | |

Note:
pKa values with a superscript "a" are beyond the scope claimed herein.

The concentration of weak base is 0.001 mol/L-1 mol/L, preferably 0.01-0.5 mol/L.

In another embodiment, the method comprises the following steps:

at room temperature, adding a weak base solution to a water solution or a mixture solution of water and organic solvent(s) containing the compound of formula I, and adjusting the pH value, thereby obtaining the compound of formula II.

As used herein, "relative retention time" means, in the HPLC analysis, the ratio of the retention time of the impurity to main peak retention time of the main peak micafungin.

As used herein, the room temperature means 0-30° C., preferably 5-20° C.

As is mentioned in the Description, the aforementioned/aforesaid feature, or the features mentioned in the examples, can be combined in any form. All features disclosed in the present description can be used in combination with any form of composition. Each features disclosed in the Description can be substituted by any substitutive features that provides equal, equivalent or similar purposes. Therefore, unless otherwise stated, the revealed features are all but general examples of equivalent or similar features.

Major advantages of the invention are listed as follows.

1. The Invention provided a preparation method for micafungin sodium which can effectively prevent new purities from generating, thereby simplifying the further purification.

2. The purification steps in the method provided by the Invention have many advantages, such as mild conditions and manageable pH values. Therefore, there is no high requirement for the equipment and the production cost can be reduced.

3. The method provided in the Invention, by which sodium type of micafungin can be obtained, not only facilitates quality control, but also is beneficial for the industrialized large-scale production.

The present invention will be further illustrated below with reference to specific examples. It should be understood that these examples are not to limit the scope of the present invention, rather to illustrate it. The experimental methods with no specific conditions described in the following examples are generally performed under conventional conditions, or according to manufacturers' instructions. Unless otherwise noted, all percentages, ratios, rates or portions used hereinafter are calculated in mass.

Units of the weight-volume percentages in the present invention are those known by the skilled in the art, such as weight of solute in 100 ml solution.

Unless otherwise defined, all professional and scientific terminologies used herein are equal in meaning to those known by the skilled in the art. In addition, any methods or material similar or equivalent to the recorded description can be used in the Invention. The preferable embodiments and materials described herein are but for the purposes of demonstration.

The method for measuring HPLC purity of Formula I compound is shown as follows.

HPLC analytical column: YMC-ODS 250×4.6 mm, 5 μm
Mobile phase: acetonitrile: phosphate buffer (pH 3.0)=70:45
Speed: 1.15 ml/min
Column temperature: 35±5° C.
Operation time: 50 min
Dilution: phosphate buffer in water
Wave length detected: 210 nm
Volume of sample injection: 10 μl
Retention time of the main peak: approx. 18 min.

Example 1

Preparation for Micafungin (Compound of Formula I)

According to synthesis process of micafungin in WO2004014879, about 10.00 g of micafungin diisopropylethylamine was prepared. Diisopropylethylamine was removed through ion exchange by using cation exchange resin UBK510L. Fractions products were collected and concentrated to obtain the compound of formula I. HPLC purity thereof was determined as 99.55% (See FIG. 1).

Comparative Example 2

Preparation for Micafungin Sodium (Compound of Formula II)

According to the purification process for micafungin in WO2004014879, ion exchange was applied to 0.5 g of compound of formula I by using 50 ml of cation exchange resin UBK510L. The product was sampled and analyzed. HPLC purity was determined as 99.54%. Then, at room temperature, 0.1 mol/L NaOH solution was slowly added dropwise with stirring, until the pH of the solution achieving 4.0. The product was sampled and analyzed. HPLC purity was determined as 98.01% (See FIG. 2). 0.1 mol/L NaOH solution was continually added dropwise until the pH achieving 4.5. The produce was sampled and analyzed. HPLC purity was determined as 97.90%. 0.1 mol/L NaOH solution was continually added dropwise till the solution pH achieving 5.0. The product was sampled and analyzed. HPLC purity was determined as 97.81%. 0.1 mol/L NaOH solution was continually added dropwise till the solution pH achieving 5.5. The product was sampled and analyzed. HPLC purity was determined as 97.75%. 0.1 mol/L NaOH solution was continually added dropwise till the solution pH achieving 6.0. The product was sampled and analyzed. HPLC purity was determined as 97.67%. 0.1 mol/L NaOH solution was continually added dropwise until the solution pH achieving 6.5. The product was sampled and analyzed. HPLC purity was determined as 97.59%. 0.1 mol/L NaOH solution was continually added dropwise until the solution pH achieving 7.0. The product was sampled and analyzed. HPLC purity was determined as 97.30%, as shown in FIG. 3.

Example 3

Preparation for Micafungin Sodium (Compound of Formula II)

0.2 g of the compound of formula I obtained in Example 1 was dissolved in 20 ml purified water. At room temperature, 0.01 mol/L sodium bicarbonate solution was slowly added dropwise with stirring until the pH achieving 4.5. The product was sampled and analyzed. HPLC purity was determined as 99.55%.

Example 4

Preparation for Micafungin Sodium (Compound of Formula II)

Figure 4:
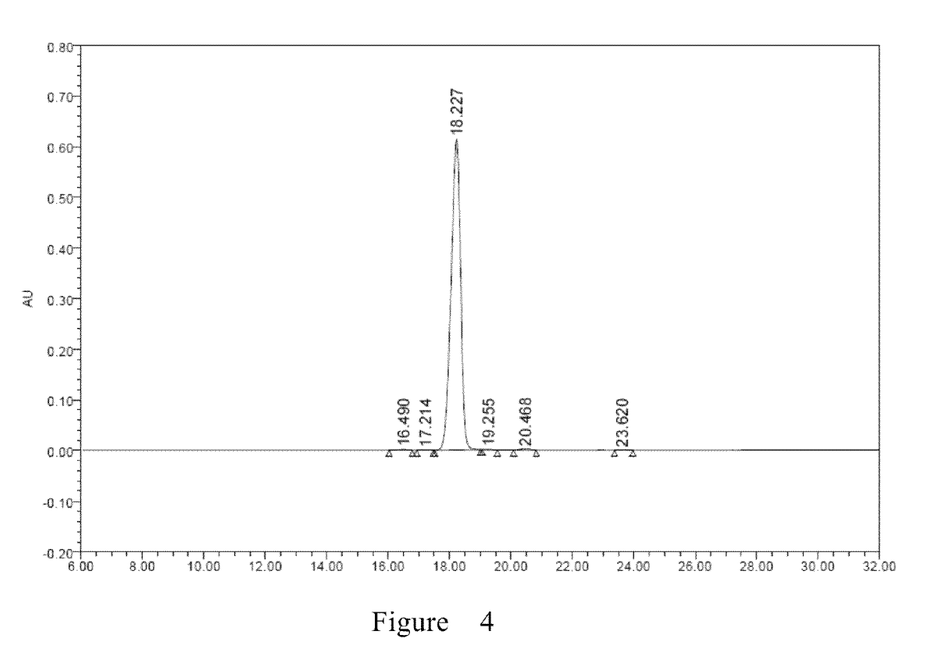
FIG. 4 is the HPLC chromatogram of formula II compound prepared in Example 4, wherein parameters of the related peaks, such as Retention Time and areas thereof are listed in the following table.

0.2 g of compound of formula I obtained from Example 1 was dissolved in 20 ml purified water. At room temperature, 0.001 mol/L sodium carbonate solution was slowly added dropwise with stirring until the pH achieving 7.0. The product was sampled and analyzed. HPLC purity was determined as 99.17%. See FIG. 4.

Example 5

Preparation for Micafungin Sodium (Compound of Formula II)

Figure 5:
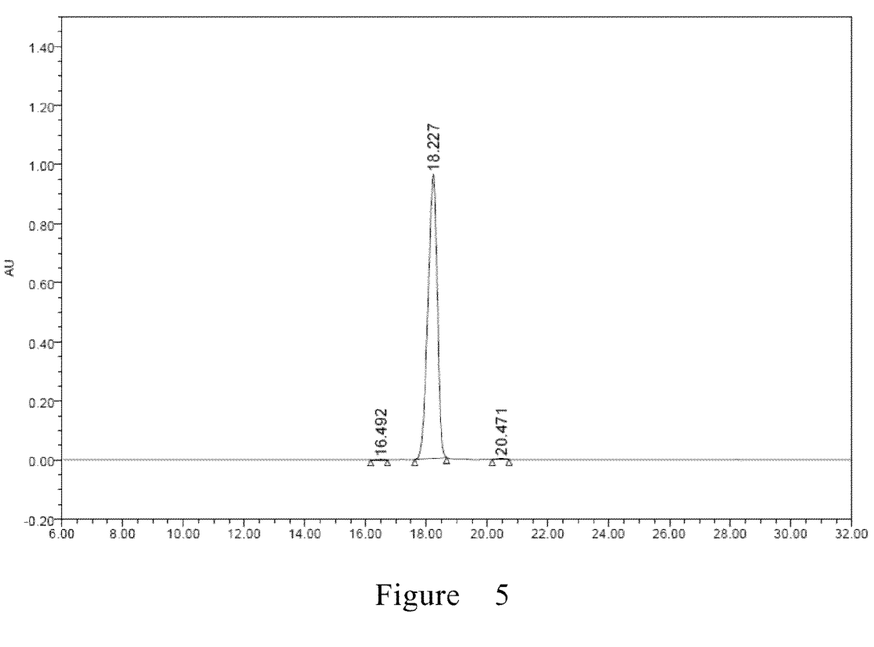
FIG. 5 is the HPLC chromatogram of formula II compound prepared in Example 5, wherein parameters of the related peaks, such as Retention Time and areas thereof are listed in the following table.

0.25 g of compound of formula I obtained from Example 1 was dissolved in 20 ml purified water. At room temperature, 0.1 mol/L mixture solution of disodium hydrogen citrate and citrate sodium (molar ratio being 1:1) was slowly added dropwise with stirring until the pH achieving 4.0. The product was sampled and analyzed. HPLC purity was determined as 99.52%. See FIG. 5.

Example 6

Preparation for Micafungin Sodium (Compound of Formula II)

0.25 g of compound of formula I obtained from Example 1 was dissolved in 20 ml purified water. At room temperature, 0.5 mol/L citrate sodium solution was slowly added dropwise with stirring until the pH achieving 5.0. The product was sampled and analyzed. HPLC purity was determined as 99.50%.

Example 7

Preparation for Micafungin Sodium (Compound of Formula II)

0.25 g compound of formula I obtained from Example 1 was dissolved in 20 ml purified water. At room temperature, 0.5 mol/L sodium oxalate solution was slowly added dropwise with stirring until the pH achieving 4.0. The product was sampled and analyzed. HPLC purity was determined as 99.52%.

Example 8

Preparation for Micafungin Sodium (Compound of Formula II)

0.25 g of compound of formula I obtained from Example 1 was dissolved in 20 ml purified water and 20 ml methanol. At room temperature, 1 mol/L sodium acetate solution was slowly added dropwise with stirring until the pH achieving 4.5. The product was sampled and analyzed. HPLC purity was determined as 99.53%.

Example 9

Preparation for Micafungin Sodium (Compound of Formula II)

0.25 g of compound of formula I obtained from Example 1 was dissolved in 20 ml purified water and 20 ml isopropanol. At room temperature, 0.5 mol/L sodium sulfite solution was slowly added dropwise with stirring until the pH achieving 5.5. The product was sampled and analyzed. HPLC purity was determined as 99.48%.

Example 10

Preparation for Micafungin Sodium (Compound of Formula II)

0.25 g of compound of formula I obtained from Example 1 was dissolved in 20 ml purified water and 20 ml n-propanol. At room temperature, 0.3 mol/L sodium hydrosulfide solution was slowly added dropwise with stirring until the pH achieving 6.0. The product was sampled and analyzed. HPLC purity was determined as 99.38%.

Example 11

Preparation for Micafungin Sodium (Compound of Formula II)

0.25 g of compound of formula I obtained from Example 1 was dissolved in 20 ml purified water and 5 ml sec-butanol. At room temperature, 0.1 mol/L mixture solution of sodium butyrate and sodium isobutyrate (molar ratio being 1:1) was slowly added dropwise with stirring until the pH achieving 4. The product was sampled and analyzed. HPLC purity was determined as 99.53%.

Example 12

Preparation for Micafungin Sodium (Compound of Formula II)

0.25 g of compound of formula I obtained from Example 1 was dissolved in 20 ml purified water and 20 ml tert-butanol. At room temperature, 0.5 mol/L disodium hydrogen phosphate solution was slowly added dropwise with stirring until the pH achieving 6.0. The product was sampled and analyzed. HPLC purity was determined as 99.40%.

Example 13

Preparation for Micafungin Sodium (Compound of Formula II)

0.25 g of compound of formula I obtained from Example 1 was dissolved in 20 ml purified water and 20 ml n-butanol. At room temperature, 0.5 mol/L sodium borate solution was slowly added dropwise with stirring until the pH achieving 6.5. The product was sampled and analyzed. HPLC purity was determined as 99.30%.

Example 14

Preparation for Micafungin Sodium (Compound of Formula II)

0.22 g of compound of formula I from Example 1 was dissolved in 20 ml purified water and 20 ml ethanol. At room temperature, 0.4 mol/L mixture solution of monosodium succinate, disodium succinate and sodium tartrate (molar ratio being 1:1:1) was slowly added dropwise with stirring until the pH achieving 4.0. The product was sampled and analyzed. HPLC purity was determined as 99.53%.

Example 15

Preparation for Micafungin Sodium (Compound of Formula II)

0.22 g of compound of formula I from Example 1 was dissolved in 20 ml purified water and 20 ml methanol. At room temperature, 0.05 mol/L mixture solution of sodium bicarbonate and sodium acetate (molar ratio being 1:1) was slowly added dropwise with stirring until the pH achieving 4.5. The product was sampled and analyzed. HPLC purity was determined as 99.54%.

Example 16

Preparation for Micafungin Sodium (Compound of Formula II)

0.22 g of compound of formula I from Example 1 was dissolved in 20 ml purified water and 20 ml methanol. At room temperature, 0.2 mol/L mixture solution of sodium sorbate and sodium malate (molar ratio being 1:1) was slowly added dropwise with stirring until the pH achieving 4.0. The product was sampled and analyzed. HPLC purity was determined as 99.49%.

Example 17

Preparation for Micafungin Sodium (Compound of Formula II)

0.22 g of compound of formula I from Example 1 was dissolved in 20 ml purified water and 20 ml methanol. At room temperature, 0.2 mol/L mixture solution of sodium propionate and sodium benzoate (molar ratio being 1:1) was slowly added dropwise with stirring until the pH achieving 4.0. The product was sampled and analyzed. HPLC purity was determined as 99.52%.

Descriptions hereinbefore are merely preferable examples and these examples are not to limit the scope of the Invention. The virtual technical content of the present invention is broadly defined in the claims sought for protection of the present invention. Should any technical entity or method accomplished by anyone else be equivalent to the scope of protection defined by the present invention, it shall be deemed as an equivalent substitution, all of which shall be deemed as encompassed in the scope of claims of the present invention.

The invention claimed is:

1. A method for the preparation of the compound of formula II, wherein said method comprises:
   mixing a weak base solution with a water solution containing the compound of formula I or a mixture solution of water and organic solvent(s) containing the compound of formula I to obtain the compound of formula II:

2. The method of claim 1, wherein pKA value of the conjugate acid corresponding to said weak base is 4-11.

3. The method of claim 2, wherein pKA value of the conjugate acid corresponding to said weak base is 5-8.

4. The method of claim 3, wherein said weak base is selected from the group consisting of disodium hydrogen citrate, sodium citrate, sodium acetate, sodium propionate, sodium butyrate, sodium isobutyrate, sodium tartrate, sodium oxalate, sodium benzoate, sodium sorbate, sodium malate, monosodium succinate, disodium succinate and combinations thereof.

5. The method of claim 4, wherein said weak base is selected from the group consisting of disodium hydrogen citrate, sodium citrate, sodium acetate and combinations thereof.

6. The method of claim 3, wherein said weak base is selected from the group consisting of sodium bicarbonate, sodium carbonate, disodium hydrogen phosphate, sodium borate, sodium sulfite, sodium hydrosulfide and combinations thereof.

7. The method of claim 6, wherein said weak base is sodium bicarbonate.

8. The method of claim 1, wherein the pH value of the solution upon mixing is 4.0-7.0.

9. The method of claim 8, wherein the pH value is 4.0-6.0.

10. The method of claim 9, wherein the pH value is 4.5-5.5.

11. The method of claim 1, wherein the concentration of said weak base solution is 0.001-1 mol/L.

12. The method of 11, wherein the concentration of said weak base solution is 0.01-0.5 mol/L.

13. The method of claim 1, wherein the organic solvent is selected from alcohols or acetonitrile.

14. The method of claim 13, wherein the organic solvent is selected from C1-C4 alcohol.

15. The method of claim 14, wherein the organic solvent is selected from the group consisting of methanol, ethanol, isopropanol, n-propanol, n-butanol, sec-butanol, t-butanol, and combinations thereof.

16. The method of claim 1, wherein the method comprises the following steps:
   at room temperature, adding the weak base solution to the water solution or the mixture solution of water and organic solvent(s) containing the compound of Formula I,
   adjusting the pH value of the obtained solution, thereby obtaining the compound of Formula II.

17. The method according to claim 14, wherein said addition is performed slowly and dropwise with stirring.

* * * * *